(12) United States Patent
Farazi et al.

(10) Patent No.: US 7,245,968 B1
(45) Date of Patent: Jul. 17, 2007

(54) IMPLANTABLE CARDIAC DEVICE PROVIDING RAPID PACING T WAVE ALTERNAN PATTERN DETECTION AND METHOD

(75) Inventors: Taraneh Farazi, San Jose, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 151 days.

(21) Appl. No.: 10/868,240

(22) Filed: Jun. 14, 2004

Related U.S. Application Data

(63) Continuation-in-part of application No. 10/186,069, filed on Jun. 28, 2002, now Pat. No. 7,027,867.

(51) Int. Cl.
*A61N 1/365* (2006.01)

(52) U.S. Cl. .............................. 607/25; 607/9; 607/14

(58) Field of Classification Search ............... 607/9, 607/25, 26; 600/508, 509, 517
See application file for complete search history.

(56) References Cited

U.S. PATENT DOCUMENTS

| 4,556,062 A | 12/1985 | Grassi et al. ......... 128/419 PG |
| 4,802,491 A | 2/1989 | Cohen et al. ............... 128/702 |
| 4,974,598 A * | 12/1990 | John ........................... 600/509 |
| 5,148,812 A | 9/1992 | Verrier et al. .............. 128/704 |
| 5,197,480 A | 3/1993 | Gebhardt .................... 128/697 |
| 5,265,617 A | 11/1993 | Verrier et al. .............. 128/704 |
| 5,300,092 A | 4/1994 | Schaldach .................. 607/18 |
| 5,466,254 A | 11/1995 | Helland ...................... 607/123 |
| 5,476,483 A | 12/1995 | Bornzin et al. ............... 607/17 |
| 5,547,285 A | 8/1996 | Hutzel et al. ................. 384/15 |
| 5,549,650 A | 8/1996 | Bornzin et al. ............... 607/24 |
| 5,560,370 A | 10/1996 | Verrier et al. .............. 128/705 |
| 5,570,696 A | 11/1996 | Arnold et al. .............. 128/707 |
| 5,842,997 A | 12/1998 | Verrier et al. ............... 600/518 |
| 5,921,940 A | 7/1999 | Verrier et al. ............... 600/518 |
| 6,016,443 A | 1/2000 | Ekwall et al. .............. 600/519 |
| 6,058,328 A * | 5/2000 | Levine et al. ................. 607/14 |
| 6,169,919 B1 * | 1/2001 | Nearing et al. ............. 600/518 |

(Continued)

FOREIGN PATENT DOCUMENTS

WO    WO 02/034123 A2    2/2002

(Continued)

OTHER PUBLICATIONS

David J. Christini, et al., "Endocardial Detection of Repolarization Alternans," *IEE Transactions on Biomedical Engineering*, vol. 50, No. 7 (2003), pp. 855-862.

*Primary Examiner*—Carl Layno
*Assistant Examiner*—Eric D. Bertram

(57) ABSTRACT

An implantable cardiac device that delivers electrical therapy to a patient's heart determines if a T wave alternan pattern of the patient's heart exists. The device includes a sensing circuit that generates an electrical signal including T waves representing paced electrical activity of the heart and a morphology detector that measures a metric of each T wave in the electrical signal. A T wave alternan pattern detector determines, responsive to the measured T wave metrics, if a paced activity T wave alternan pattern is present. The T wave alternan pattern detector may also detect for intrinsic T wave alternan patterns. A therapy control initiates suitable different responses for a paced T wave alternan pattern detection and an intrinsic T wave alternan pattern detection.

13 Claims, 5 Drawing Sheets

U.S. PATENT DOCUMENTS

| | | |
|---|---|---|
| 6,253,107 B1 | 6/2001 | Albrecht et al. ............... 607/9 |
| 6,493,586 B1 | 12/2002 | Stahmann et al. ............ 607/27 |
| 6,823,213 B1 * | 11/2004 | Norris et al. .................. 607/9 |
| 6,915,156 B2 * | 7/2005 | Christini et al. ............ 600/509 |
| 2001/0007948 A1 | 7/2001 | Stoop et al. .................. 607/14 |
| 2002/0138106 A1 | 9/2002 | Christini et al. ............... 607/9 |
| 2003/0060854 A1 | 3/2003 | Zhu ............................ 607/25 |

FOREIGN PATENT DOCUMENTS

| | | |
|---|---|---|
| WO | WO 02/034123 A3 | 2/2002 |

* cited by examiner

IMPLANTABLE CARDIAC DEVICE PROVIDING RAPID PACING T WAVE ALTERNAN PATTERN DETECTION AND METHOD

CROSS REFERENCE TO RELATED APPLICATIONS

This application is a continuation-in-part of U.S. patent application Ser. No. 10/186,069, filed Jun. 28, 2002 now U.S. Pat. No. 7,027,867, title "Implantable Cardiac Device Having a System for Detecting T-Wave Alternan Patterns and Method."

FIELD OF THE INVENTION

The present invention generally relates to an implantable cardiac device that delivers electrical therapy to a patient's heart. The present invention more particularly relates to such a device capable of detecting T wave alternan patterns.

BACKGROUND OF THE INVENTION

Implantable cardiac stimulation devices are well known in the art. They include implantable pacemakers which provide stimulation pulses to a heart to cause a heart, which would normally or otherwise beat too slowly or at an irregular rate, to beat at a controlled normal rate. They also include defibrillators which detect when the atria and/or the ventricles of the heart are in fibrillation and apply cardioverting or defibrillating electrical energy to the heart to restore the heart to a normal rhythm. Implantable cardiac stimulation devices may also include the combined functionalities of a pacemaker and a defibrillator.

As is well known, implantable cardiac stimulation devices sense cardiac activity for monitoring the cardiac condition of the patient in which the device is implanted. By sensing the cardiac activity of the patient, the device is able to provide cardiac stimulation therapy when it is required.

As is well known, a cardiac cycle on an electrocardiogram (ECG) extends from one heart beat (QRS complex) to the next. During each cardiac cycle, a T wave occurs. The T wave is a low-frequency wave that follows the ST-segment and represents repolarization of the ventricular myocardium. Alternate occurring T wave amplitudes (i.e., high/low amplitudes occurring at odd/even beats) are referred to as T wave alternans (TWAs).

T wave alternan patterns are known to be a precursor for sudden cardiac death. In the past, detection of T wave alternan patterns has been performed using surface ECGs. Implementation of such detection has included the measurement, on a beat-to-beat basis, of the micro-volt level changes in the T wave amplitude from the surface ECG. Then, the long record of time series of T wave amplitude change is transformed into the frequency domain by Fourier series transformation (FFT). A prominent peak in the FFT at 0.5 Hz would verify the existence of a T wave alternan pattern.

Unfortunately, the above detection method requires the use of medical equipment that must be operated by medical personnel in a medical facility such as a physician's office. The detection requires long term recording of surface ECGs and off-line analysis with robust computation equipment. As a result, T wave alternan pattern monitoring has been inconvenient and cumbersome. As a result, it is difficult to provide continuous and regular T wave alternan pattern monitoring.

Many patients who would benefit from T wave alternan pattern monitoring have an implanted cardiac device such as an implantable defibrillator or a combined defibrillator pacemaker. It would thus be highly desirable if such an implanted device could detect for T wave alternan patterns. However, the prior art detection method does not lend itself for such application due to, for example, the required long term monitoring, surface ECG, and robust computational requirements for Fourier series transformation.

In order for an implanted cardiac device to provide T wave alternan pattern monitoring, there is a need for a new and different approach. With such a new approach, it would be possible to provide arrhythmia risk assessments on demand and more timely delivery of preventative therapy.

SUMMARY

What is described herein is an implantable cardiac stimulation device comprising a pulse generator that applies pacing pulses to a heart at a pacing rate above an intrinsic rate, a sensing circuit that generates an electrical signal including T waves representing paced electrical activity of the heart responsive to the pacing pulses, and a morphology detector that receives the electrical signal from the sensing circuit and that measures a metric of each T wave in the electrical signal. The device further includes a T wave alternan pattern detector that receives the measured T wave metrics from the morphology detector and that determines, responsive to the measured T wave metrics, if a paced activity T wave alternan pattern is present.

The pulse generator preferably provides the pacing pulses at a first rate and thereafter provides the pacing pulses at a second rate responsive to the T wave alternan pattern detector failing to detect a T wave alternan pattern when the pacing pulses are applied to the heart at the first rate. The second rate is preferably higher than the first rate.

The device may further include a heart rate measuring circuit that measures heart rate of the heart. The pulse generator may then apply the pacing pulses at the pacing rate above an intrinsic rate if the heart rate measuring circuit measures a heart rate below a given rate.

The sensing circuit may generate an intrinsic electrical activity signal including T waves. The morphology detector may then receive the intrinsic electrical activity signal and measure the metric of the intrinsic electrical activity signal T waves. The T wave alternan pattern detector may receive the measured intrinsic T wave metrics and determine if an intrinsic activity T wave alternan pattern is present.

The heart rate measuring circuit may enable the sensing circuit to generate the intrinsic electrical activity signal if the heart rate is above a predetermined accelerated heart rate. The device may further include a therapy control that initiates a first therapy responsive to detection of a paced activity T wave alternan pattern and a second therapy responsive to detection of an intrinsic activity T wave alternan pattern. The second therapy response is preferably more aggressive than the first therapy response.

In another embodiment, an implantable cardiac device comprises a T wave alternan pattern monitor that detects overdrive paced T wave alternan patterns and high rate intrinsic T wave alternan patterns. A therapy control initiates a first responsive therapy when an overdrive paced T wave alternan pattern is detected and a second responsive therapy when a high rate intrinsic T wave alternan pattern is detected.

In another embodiment, a method comprises applying pacing pulses to a heart at a pacing rate above an intrinsic rate, generating an electrical signal including T waves representing paced electrical activity of the heart responsive to the pacing pulses, measuring a metric of each T wave in the electrical signal, and determining, responsive to the measured T wave metrics, if a paced activity T wave alternan pattern is present.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
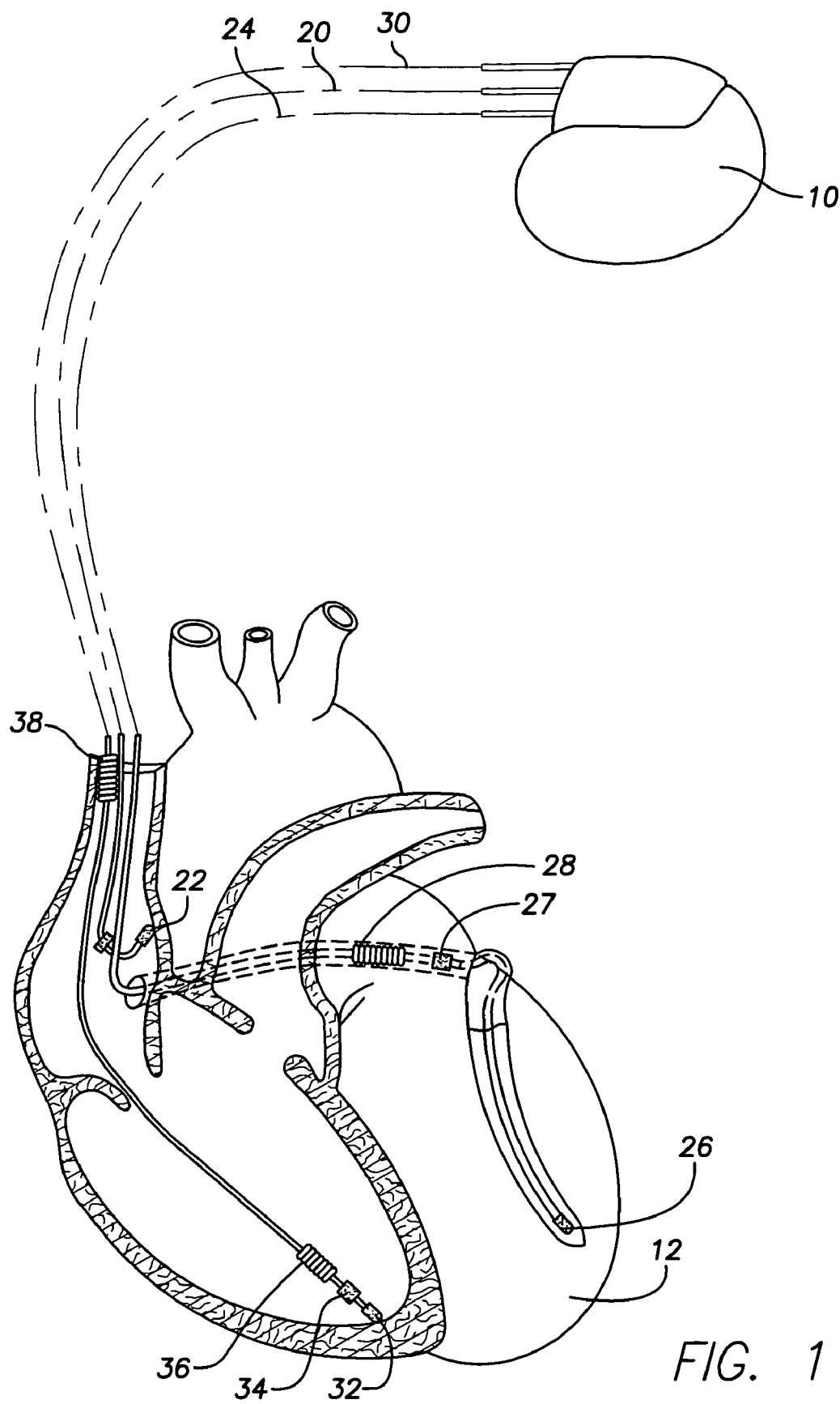
FIG. 1 is a simplified diagram illustrating an implantable stimulation device embodying the present invention in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. Pat. No. 5,466,254, "Coronary Sinus Lead with Atrial Sensing Capability" (Helland), which patent is hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
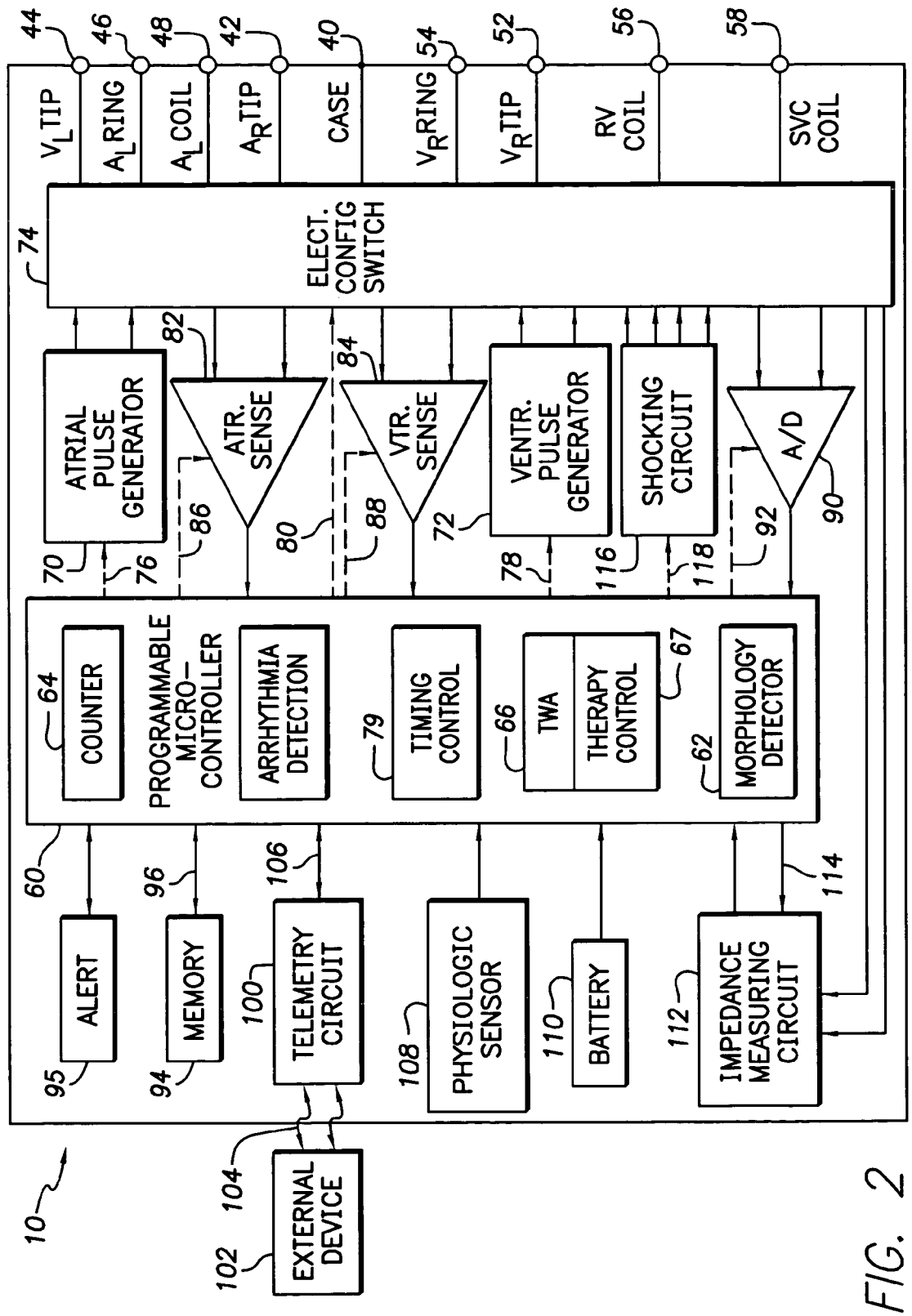
FIG. 2 is a functional block diagram of the device of FIG. 1 illustrating the basic elements thereof which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art. In accordance with the present invention, the timing control 79 may also be employed to time spaced apart times for activating T wave alternan pattern detection a TWA detection periods.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes. Advantageously, the data acquisition system 90 may be utilized in acquiring data for T wave alternan pattern detection in accordance with the present invention as more particularly described subsequently.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. The memory 94 may further be used to store data associated with T wave alternan pattern detection in accordance with the present invention. That data may include, for example, heart rate, time of T wave alternan pattern detection, TWA test outcomes and measured T wave metrics.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the device 10 has been generally described, those elements and features of the device which more particularly pertain to this embodiment will now be described. During the T wave alternan pattern detection, a T wave metric of each T wave of a plurality of cardiac cycles counted by a counter 64 is measured. The predetermined T wave metric may be, for example, T wave amplitude. To this end, the data acquisition system 90 preferably includes a sensing circuit having a sensitivity in the range of 0.3 mV to 10 mV for example. The counter 64 is employed to be assured that a minimum of cardiac cycles are used in the TWA pattern detection.

Further, the lead system of FIG. 1 offers a plurality of different T wave sensing electrode configurations. Those configurations include, for example, the left ventricular tip electrode 26 with either the right ventricular tip electrode 32 or the right ventricular ring electrode 34. Other possible electrode configurations include the case 40 and either the right ventricular tip electrode 32 or the right ventricular ring electrode 34 or the right ventricular coil electrode 36 and the left ventricular tip electrode 26. Here, the switch 74 may be used to advantage in permitting the selection of the T wave sensing electrode configuration that maximizes the magnitude of the predetermined T wave metric to be measured.

For measuring the T wave metric, the microcontroller includes a morphology detector 62. When the predetermined T wave metric is T wave amplitude, the morphology detector 62 may be used to measure the T wave amplitudes. Other T wave metric amplitudes such as T wave slope may be measured as needed from the electrogram signal generated by the acquisition system 90.

To detect the TWA patterns, the microcontroller includes a TWA detector 66. As will be seen hereinafter, the TWA detector determines the average T wave amplitude of the odd numbered T waves and the average T wave amplitude of the even numbered T waves. The difference between the averages is used to determine if a TWA pattern is present as described subsequently in connection with the flow charts of FIGS. 3–5.

Alternatively, to determine if a TWA pattern exists, the TWA detector may determine the difference between T wave amplitude of every successive beat in a sliding window of length N beats (e.g., N=100 beats). The detector then may create a histogram of the T wave amplitude differences in each sliding window. The TWA detector may then determine if the shape of the histogram forms a "double peak mountain" or an upside down "W" centered at about zero. The detector may make this determination, for example, by searching for local maxima's within the histogram. When two local maxima's are found at opposite polarities, for example, at around +/−0.1 mV, TWA detection is positive.

Alternatively, power spectral analysis can be used to determine T wave alternans. This approach is described in detail in the article: IEEE Transactions on Biomedical Engineering, v. 50, no. 7, July 2003 pp. 855–861.

To report the results of a T wave alternan pattern detection, the telemetry circuit 100 may be employed. After each detection, the presence or absence of a detected T wave alternan pattern may be stored in memory 94 along with other information associated with the detection. The associated data may include heart rate and the time of the detection. The memory 94 may further include two histograms, one histogram for the T wave amplitudes when there is no detected T wave alternan pattern and the other for the T wave amplitudes when there is a detected T wave alternan pattern. The histograms enable the physician to see the distribution of the T wave amplitudes. Once stored in memory 94, the data is available for transmission by telemetry circuit 100 to an external receiver 102 for display at follow-up, for example.

The device 10 further includes an alert 95. The alert may be activated when one or more T wave alternan patterns are detected. The alert may take the form of any device capable of providing an output or indication perceptible by the patient. To this end, the alert 95 may be a speaker or a vibrator, for example.

TWA pattern detection may be initiated, according to this embodiment at desired times on demand or when the heart rate exceeds a set accelerated rate. If initiated on demand, the TWA detection is supported by overdrive pacing, such as overdrive atrial pacing, at a rate above the intrinsic rate as determined by the timing control 79 and the activity sensor 108. Prior to such pacing however, the heart rate is determined and if it is greater than a selected accelerated rate, the TWA detection is aborted to prevent overdrive pacing into an already accelerated heart rhythm. If the heart rate is below the selected accelerated rate, the TWA pattern detection begins with the overdrive pacing of an atrium of the heart.

If T wave alternans are not detected within the detection window, the pacing rate is increased and a new detection window is started. Any number of rate increases in any desired increments may be used. When no paced activity T wave alternans are detected at any tested rate, the outcome is reported as negative. If T wave alternans are detected within a detection window, the TWA detector then determines if there is a sustained TWA pattern. If T wave alternans are not a sustained pattern, the outcome is reported as indeterminate. If a sustained paced activity TWA pattern is detected, the outcome is reported as positive.

If the detection is enabled because the intrinsic rate exceeds the set accelerated rate, the intrinsic activity TWA pattern detection is initiated. The TWA pattern detection continues until a preselected number of cardiac cycles have been monitored or until the intrinsic rate falls below the set rate. If the heart rate falls below the set rate, an assessment for a TWA pattern is made as long as some minimum number of cardiac cycles have been monitored during the elevated heart rate.

Hence, a paced activity TWA pattern or an intrinsic activity TWA pattern may be detected. If a paced activity TWA pattern is detected, a first responsive therapy may be initiated by therapy control 67. If an intrinsic activity TWA pattern is detected, a second responsive therapy may be initiated by the therapy control.

The first responsive therapy consistent with an elevated risk of arrhythmia may include, for example, long term preventive pacing therapy, warning or alerting the patient or physician, or the upgrading to an implantable device capable of defibrillation.

The second responsive therapy, consistent with a very high risk of imminent arrhythmia, may include more aggressive therapy such as, for example, the preparation for delivery of a defibrillation shock or aggressive overdrive pacing with attempted gradual return to a resting cardiac rate.

Figure 3:
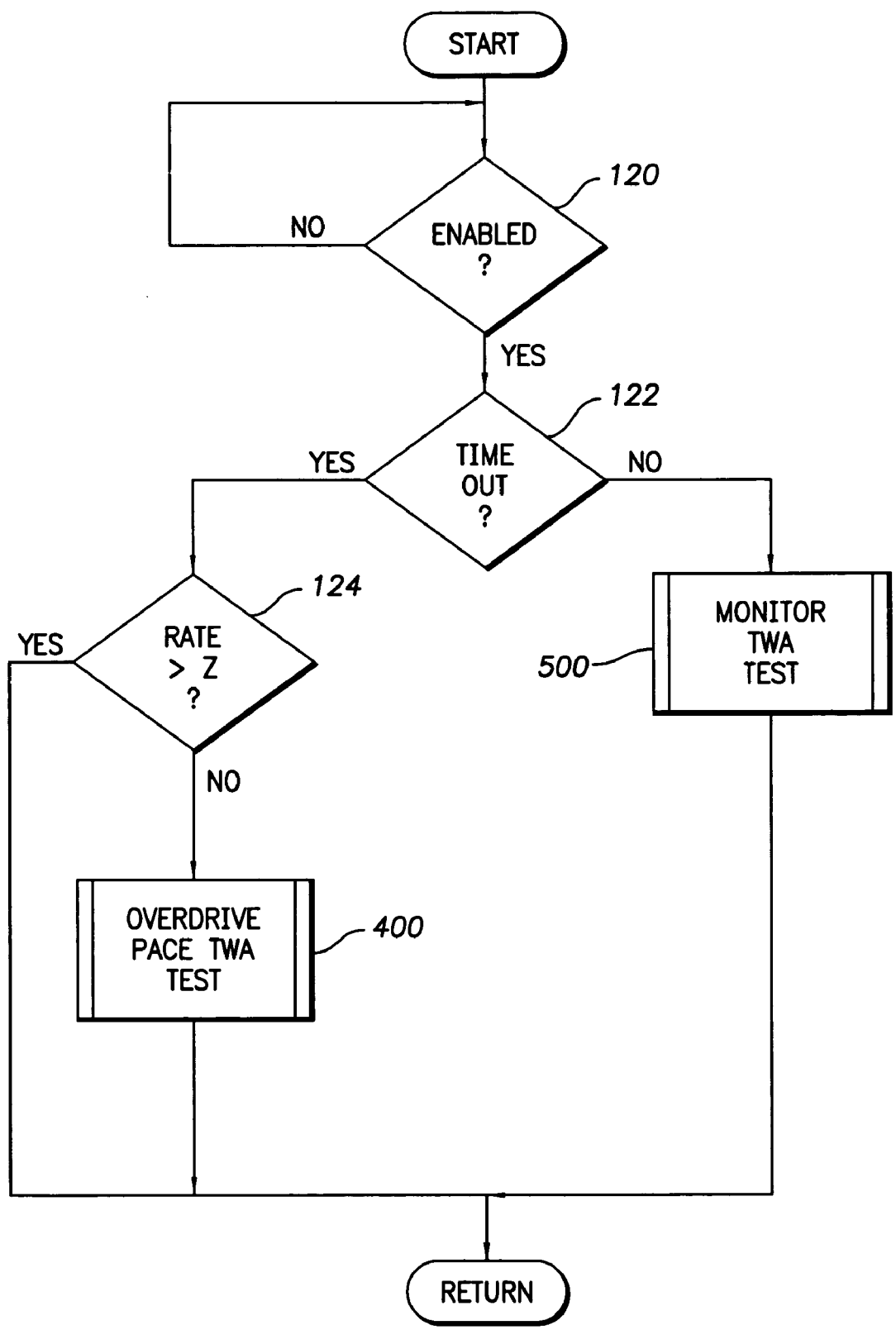
FIG. 3 is a flow chart describing an overview of the operation of one embodiment of the present invention.

In FIG. 3, a flow chart is shown describing an overview of the operation and novel features implemented in one embodiment of the device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The T wave alternan pattern detection, in accordance with this embodiment of the present invention, initiates in FIG. 3 at decision block 120. In accordance with decision block 120, the T wave alternan detector 66 determines if it has been enabled. If it has not, the process returns. If, however, the T wave alternan detector 66 determines in accordance with decision block 120 that it has been enabled, the process advances to decision block 122 wherein the T wave alternan detector 66 determines if it has been enabled because of a time timeout or because it has been triggered by the cardiac rate exceeding the accelerated set rate. If the T wave alternan detector 66 has been enabled due to a timeout, the process then advances to decision block 124 wherein it is determined if the current cardiac rate is above a predetermined selected rate (Z). If the current cardiac rate is above the accelerated selected rate, the process returns. This aborts the T wave alternan pattern detection to avoid overdrive pacing the heart when it is already at an accelerated rate. The selected accelerated rate is of course above a normal rate at rest, and may be, for example, 105 beats per minute.

If in decision block 124 it is determined that the current cardiac rate is less than the predetermined accelerated set rate, the process then advances to subroutine 400 for providing the overdrive pace T wave alternan pattern test 400. The overdrive pace T wave alternan pattern test 400 will be described in detail subsequently with reference to FIG. 4. Once the test is completed, the process returns.

If in decision block 122 it is determined that the T wave alternan detector was not enabled due to a timeout but because the cardiac rate exceeded the predetermined set rate of, for example, 110 beats per minute, the process immediately advances to subroutine 500 wherein the T wave alternan pattern detector 66 performs the monitor T wave alternan pattern test. The monitor T wave alternan pattern test 500 will be described in detail hereinafter with reference to FIG. 5. Once the monitor T wave alternan pattern test is completed, the process returns.

Figure 4:
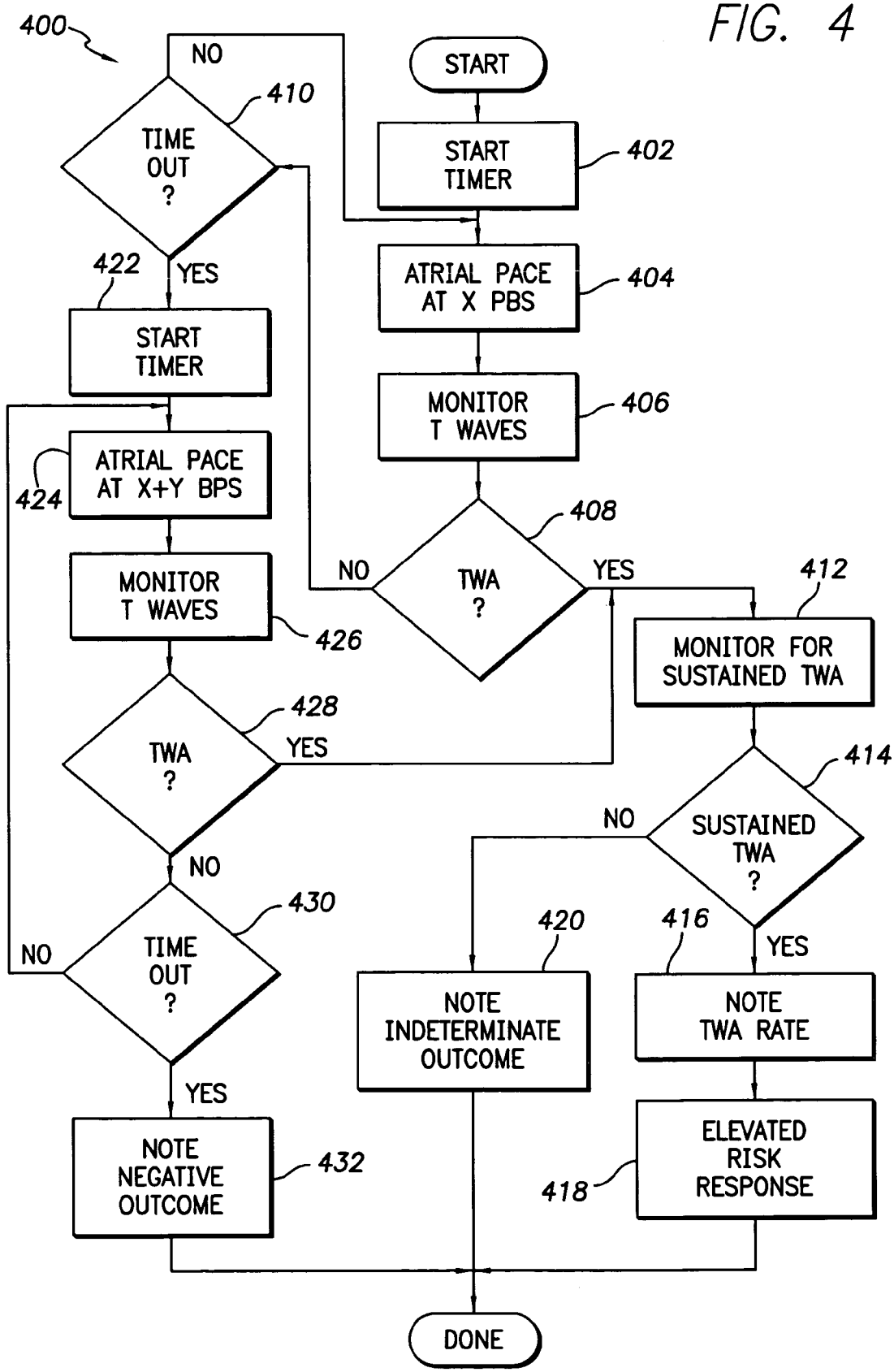
FIG. 4 is a flow diagram describing the overdrive pacing T wave alternan test subroutine of FIG. 3.

Referring now to FIG. 4, it shows a flow chart describing the overdrive pace T wave alternan pattern test subroutine 400.

The subroutine 400 initiates with activity block 402 wherein the timing control 79 starts a timer for timing a test window. As indicated by activity blocks 404 and 406, during the test window, one of the atria is overdrive paced at a rate (X) which is above the intrinsic rate of the heart as determined by the timing control 79 and the activity sensor 108. After each atrial pacing pulse, the resulting T wave is monitored. More specifically, during each atrial paced cardiac cycle, the data acquisition system 90 generates an electrical signal representing the paced ventricular activity of the heart. The electrical signal is then digitized and stored in memory 94. The morphology detector 62 then isolates the T wave stored in memory 94 in a manner known in the art and measures the T wave amplitude. After each such pacing pulse and T wave amplitude measurement, the process advances to decision block 408 wherein the T wave alternan pattern detector 66 determines if T wave alternans have been detected. In performing decision block 408, the T wave alternan pattern detector 66 averages the T wave amplitudes corresponding to the odd numbered cardiac cycles and averages the T wave amplitudes of the even numbered cardiac cycles. It then determines the difference between the T wave amplitude averages. If the T wave average difference is greater than a threshold, such as 0.1 millivolts, T wave alternans will be determined to be present.

The determination of the presence of T wave alternans requires a plurality of cardiac cycles to be monitored. For example, 100 cardiac cycles may be monitored to provide a minimum number of fifty odd numbered cardiac cycles and fifty even numbered cardiac cycles from which to make the determination in accordance with decision block 408.

If it is determined that T wave alternans are not currently present, the process advances to decision block 410 wherein it is determined if a timer started in activity block 402 has timed out. If it hasn't, the process returns to activity blocks 404 and 406 for repeating the detection of T wave alternans. If, during the window established by the timer set in activity block 402, T wave alternans are detected, the process advances to activity block 412 wherein the T wave alternan pattern detector 62 monitors for a sustained T wave alternan pattern. In accordance with activity block 412, the T wave alternan pattern detector 66 monitors the T wave amplitudes for at least one minute. After the monitoring in activity block 412, the process advances to decision block 414 wherein it is determined if there is a sustained T wave alternan pattern. Here, it is determined if the T wave alternans have lasted longer than one minute. More specifically, in accordance with decision block 414, a sustained T wave alternan pattern may be defined as alternans that are greater than 0.1 millivolts that last longer than a minute and persists above a specific heart rate threshold.

If in decision block 414 it is determined that a T wave alternan pattern is present, the process advances to activity block 416 where the pacing rate which resulted in the sustained T wave alternan pattern is stored in memory 94. Then, in activity block 418, the therapy control 67 initiates a therapy response consistent with an elevated risk of accelerated arrhythmia. The therapy response contemplated by activity block 418 may be, for example, long term preventative pacing therapy, providing a warning or alert to the patient, or upgrading the patient's implanted device with an implantable device capable of defibrillation if the patient's current implanted device does not have that functionality. The process then completes.

If in decision block 414 it is determined that there is not a sustained T wave alternan pattern, the process advances to activity block 420 wherein an indeterminate outcome notation is stored in memory 94. The process then completes.

If in decision block 410 it is determined that the test window timer has timed out, the process advances to activity block 422 wherein the T wave alternan detector 66 causes the timing control 72 to reset the test window timer. The process then advances to activity block 424 wherein the T wave alternan pattern detector 66 incrementally increases the overdrive pacing rate. The heart is now paced at the higher rate and the T waves are monitored in accordance with activity block 426 after each atrial pacing pulse. Activity blocks 424 and 426 may be implemented in the same manner as activity blocks 404 and 406 but at the incrementally increased pacing rate.

After the minimum number of cardiac cycles have been monitored, the process advances to decision block 428 where it is determined if there are T wave alternans. If there are, the process then advances to activity block 412 wherein the T wave alternan pattern detector 66 determines if there is a sustained paced T wave alternan pattern as previously described. If in decision block 428 it is determined that there are no T wave alternans at present, the process advances to decision block 430 wherein it is determined if the test window is timed out. If it is not, the process returns to activity blocks 424 and 426 for continued pacing and monitoring. However, if the timer has timed out, the process advances to activity block 432 wherein a negative outcome is noted in memory 94 and the process returns.

Figure 5:
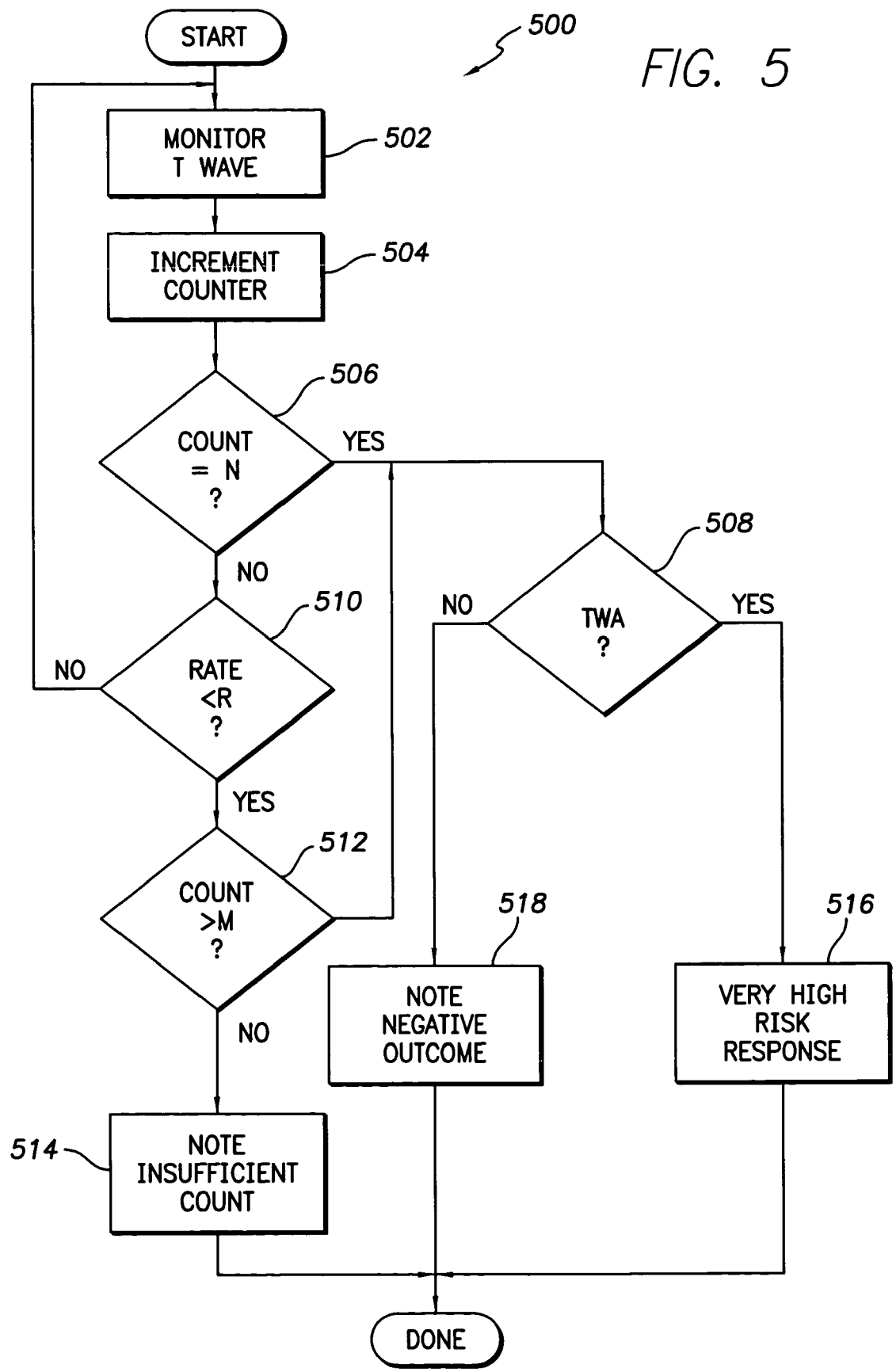
FIG. 5 is a flow diagram describing the monitor T wave alternan test subroutine of FIG. 3.

Referring now to FIG. 5, it is a flow chart describing the monitored T wave alternan pattern test subroutine 500. The subroutine 500 initiates with activity block 502 wherein the T wave of the first cardiac cycle following the enablement of the T wave alternan pattern detector 66 is monitored. Again, the T wave may be monitored by the generation of an intrinsic electrical signal by the data acquisition system 90 which is then digitized and stored in memory 94. A morphology detector 62 may then isolate the T wave from each cardiac cycle and measure its amplitude.

Once the T wave is monitored in activity block 502, the process advances to activity block 504 where a counter established by the T wave alternan pattern detector 66 is incremented. The purpose of the counter is to count the number of T waves which have been monitored to support a determination of whether a minimum number of cardiac cycles have been monitored to facilitate a T wave alternan pattern determination and a determination of whether a predetermined number of cardiac cycles have been monitored to trigger the determination of a T wave alternan pattern.

More specifically, after the counter is incremented in activity block 504, the process advances to decision block 506 wherein it is determined if the count has reached a predetermined count (N). If it has, the process advances to decision block 508 wherein it is determined if there is a T wave alternan pattern. However, if in decision block 506, it is determined that the count has not reached the predetermined count (N), the process advances to decision block 510 wherein it is determined if the cardiac rate has fallen below a selected rate. The selected rate is preferably an accelerated rate below predetermined set rate which triggered the TWA alternan pattern detection. If the rate for triggering the TWA alternan pattern detection is, for example, 105 beats per minute, the set rate (R) may be, for example, 100 beats per minute. If the rate has not decreased below the predetermined accelerated set rate (R), the process returns to activity block 502 for the monitoring of the next T wave. However, if the rate has fallen below the predetermined accelerated set rate, the process then advances to activity block 512 where it is determined if the count is greater than some minimum count (M) to enable the determination of a T wave alternan pattern. If the count is not greater than the minimum count, the process advances to activity block 514 wherein an insufficient count notation is stored in memory 94 and the process returns. However, if the count is greater than the minimum number of counts, the process then advances to decision block 518 to facilitate the determination if there is a T wave alternan pattern.

To implement decision block 508, the T wave alternan pattern detector 66 once again averages the T wave amplitudes of the odd numbered cardiac cycles and the T wave amplitudes of the even numbered cardiac cycles. It then determines the difference between the T wave amplitude averages. If the difference is greater than an intrinsic T wave alternan pattern threshold, a T wave alternan pattern will be determined to exist. The threshold may be, for example, 0.1 millivolts.

If in decision block 508, it is determined that a T wave alternan pattern exists, the process advances to activity block 516 where a responsive therapy consistent with a very high risk of imminent accelerated arrhythmia is initiated by the therapy control 67. The very high risk response may be, for example, more aggressive therapy than that initiated for the elevated risk response and may include, for example, the preparation for delivery of a defibrillation shock to the heart or aggressive overdriving pacing with eventual attempted gradual return to a resting cardiac rate. Also consistent with the very high risk response, the alert 95 may be utilized to provide a perceptible indication to the patient of the very high risk response. The process then completes. If in decision block 508 it is determined that a T wave alternan pattern does not exist, the process advances to activity block 518 wherein a negative outcome notation is stored in memory 94. The process then completes.

In view of the foregoing, it may be seen that the present invention provides an implantable cardiac device and method which facilitates on demand risk assessment of impending accelerated arrhythmias. In addition, the present invention provides such a device and method which also alerts the patient and/or physician to a potentially imminent accelerated arrhythmia and further provides a very high risk response to treat or prevent the imminent accelerated arrhythmia. Because the T wave alternan pattern detection may be carried out on a periodic basis, the effects on a patient's cardiac condition due to environmental changes or drug titration, for example, may be assessed on a continuous basis.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac device comprising:
   a T wave alternan pattern monitor that detects overdrive paced T wave alternan patterns and high rate intrinsic T wave alternan patterns; and
   a therapy control that initiates a first responsive therapy when an overdrive paced T wave alternan pattern is detected and a second responsive therapy different from the first responsive therapy when a high rate intrinsic T wave alternan pattern is detected.

2. A method comprising:
   detecting one of either overdrive paced T wave alternan patterns or high rate intrinsic T wave alternan patterns using an implantable cardiac device;
   initiating a first responsive therapy when an overdrive paced T wave alternan pattern is detected; and
   initiating a second responsive therapy different from the first responsive therapy when a high rate intrinsic T wave alternan pattern is detected.

3. The method of claim 2 wherein the first responsive therapy comprises long term preventive pacing.

4. The method of claim 2 wherein the second responsive therapy comprises at least one of defibrillation shock therapy and aggressive overdrive pacing.

5. The method of claim 2 wherein the first responsive therapy and the second responsive therapy are initiated by the implantable cardiac device.

6. The method of claim 2 wherein detecting overdrive paced T wave alternan patterns comprises:
   measuring the heart rate of a heart to obtain an intrinsic rate; and
   applying pacing pulses to the heart at a pacing rate above the intrinsic rate if the intrinsic rate is below a given accelerated rate.

7. An implantable cardiac stimulation device comprising:
   a heart rate measuring circuit operative to measure the intrinsic heart rate of a heart having a normal heart rate at rest;
   a pulse generator operative to apply pacing pulses to the heart;
   means for detecting the presence of T-wave alternans; and
   a processor operative to initiate an overdrive paced T-wave analysis by the T-wave alternans detecting means by periodically overdrive pacing the heart for a period of time if the intrinsic rate is below a set high-rate intrinsic rate that is above the normal heart rate, and to initiate an high-rate intrinsic T-wave analysis, different then the overdrive paced T-wave analysis, if the intrinsic rate is above the set high-rate intrinsic rate.

8. The device of claim 7 further comprising a therapy control that initiates a first responsive therapy when an overdrive paced T wave alternan pattern is detected and a second responsive therapy different from the first responsive therapy when a high-rate intrinsic T wave alternan pattern is detected.

9. The device of claim 8 wherein the second therapy response is more aggressive than the first therapy response.

10. The device of claim 7 wherein the means for detecting the presence of T-wave alternans comprises:
    a sensing circuit that generates an electrical signal including T waves representing electrical activity of the heart;
    a morphology detector that receives the electrical signal from the sensing circuit and that measures a metric of each T wave in the electrical signal; and
    a T wave alternan pattern detector that receives the measured T wave metrics from the morphology detector and that determines, responsive to the measured T wave metrics if a T wave alternan pattern is present.

11. The device of claim 10 wherein, for an overdrive paced T-wave analysis, the T wave alternan pattern detector determines if the overdrive paced activity T wave alternan pattern is a sustained T wave alternan pattern.

12. The device of claim 10 wherein the T wave alternan pattern detector provides a histogram of T wave amplitude difference between successive T waves occurring within a sliding window and determines if a T wave alternan pattern is present responsive to a shape in the histogram.

13. The device of claim 7 wherein the pulse generator applies pacing pulses to an atrium of the heart.

* * * * *